(12) United States Patent
Messina et al.

(10) Patent No.: US 10,299,759 B2
(45) Date of Patent: *May 28, 2019

(54) ULTRASOUND SYSTEM CONTROL PANEL AND DISPLAY LIFT

(71) Applicant: KONINKLIJKE PHILIPS N.V., Eindhoven (NL)

(72) Inventors: Mark Anthony Messina, Eindhoven (NL); David Dolan, Londonderry, NH (US); Daniel van Alphen, Eindhoven (NL); Thomas James Hunt, Eindhoven (NL); Brent Jordan, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/835,535

(22) Filed: Dec. 8, 2017

(65) Prior Publication Data

US 2018/0098751 A1    Apr. 12, 2018

Related U.S. Application Data

(63) Continuation of application No. 15/341,065, filed on Nov. 2, 2016, now Pat. No. 9,855,023, which is a (Continued)

(51) Int. Cl.
*A47K 1/04* (2006.01)
*A61B 8/00* (2006.01)
(Continued)

(52) U.S. Cl.
CPC ............ *A61B 8/462* (2013.01); *A61B 8/4405* (2013.01); *A61B 8/467* (2013.01); *F16M 11/043* (2013.01);
(Continued)

(58) Field of Classification Search
CPC ....... A61B 8/4405; A61B 8/462; A61B 8/467; F16M 11/046; F16M 11/12; F16M 11/06;
(Continued)

(56) References Cited

U.S. PATENT DOCUMENTS 6,098,936 A    8/2000   Birrell
6,298,794 B1   10/2001  Brown et al.
(Continued)

FOREIGN PATENT DOCUMENTS

EP      2092892 A1    8/2009
JP      200867794     3/2008
(Continued)

*Primary Examiner* — Gwendolyn W Baxter

(57) ABSTRACT

The control panel and display of a cart-borne ultrasound system are support by a lift which can be controlled to allow the control panel and display to be raised, lowered, and rotated. The lift has a first pivot elbow mounted to the ultrasound system cart and a second pivot elbow on which the control panel and display are mounted. A four-bar linkage is coupled between the pivot elbows which enables to control panel and display to be raised and lowered while maintaining the inclination of the control panel. The pivot elbows allow the control panel and display to be turned and rotated. A pair of hydraulic struts are mounted to the four-bar linkage to support the weight of the control panel and display. When a control button on the handle of the control panel is depressed the control panel and display can be freely raised, lowered and rotated. When the control button is released the pivot elbows and four-bar linkages are locked in their current positions.

19 Claims, 3 Drawing Sheets

Related U.S. Application Data continuation of application No. 14/652,858, filed as application No. PCT/IB2013/060993 on Dec. 16, 2013, now Pat. No. 9,504,447.

(60) Provisional application No. 61/739,529, filed on Dec. 19, 2012.

(51) Int. Cl.

| | | |
|---|---|---|
| *F16M 11/12* | (2006.01) | |
| *F16M 11/04* | (2006.01) | |
| *F16M 11/06* | (2006.01) | |
| *F16M 11/20* | (2006.01) | |
| *F16M 11/24* | (2006.01) | |
| *F16M 11/10* | (2006.01) | |
| *H01H 3/12* | (2006.01) | |
| *H01H 3/14* | (2006.01) | |
| *H01H 9/16* | (2006.01) | |
| *H01H 9/26* | (2006.01) | |
| *H05K 5/00* | (2006.01) | |

(52) U.S. Cl.
CPC ........... *F16M 11/046* (2013.01); *F16M 11/06* (2013.01); *F16M 11/10* (2013.01); *F16M 11/12* (2013.01); *F16M 11/2014* (2013.01); *F16M 11/2064* (2013.01); *F16M 11/24* (2013.01); *H01H 3/12* (2013.01); *H01H 3/14* (2013.01); *H01H 9/161* (2013.01); *H01H 9/26* (2013.01); *H05K 5/0017* (2013.01); *F16M 2200/021* (2013.01); *F16M 2200/024* (2013.01); *F16M 2200/041* (2013.01)

(58) Field of Classification Search
CPC ............... F16M 11/2014; F16M 11/24; F16M 2200/021; F16M 2200/041; F16M 11/2064; F16M 11/043; F16M 11/10; H01H 3/12; H01H 3/14; H01H 9/161; H01H 9/26; H05K 5/0017
USPC ...... 248/129, 280.11, 281.11, 581, 917, 918; 280/6.15, 43.17, 43.23; 600/437, 443, 600/447
See application file for complete search history.

(56) References Cited

U.S. PATENT DOCUMENTS

| | | | |
|---|---|---|---|
| 6,648,825 | B1 | 11/2003 | Mesaros et al. |
| 6,663,569 | B1* | 12/2003 | Wilkins .................. A61B 8/00 600/459 |
| 6,669,639 | B1 | 12/2003 | Miller et al. |
| 6,709,391 | B2 | 3/2004 | Mesaros et al. |
| 6,796,536 | B1 | 9/2004 | Sevier |
| 7,121,514 | B2 | 10/2006 | Twyford |
| 7,654,704 | B2 | 2/2010 | Zhang et al. |
| 9,039,016 | B2 | 5/2015 | Abernethy et al. |
| 2003/0220564 | A1 | 11/2003 | Wilkins et al. |
| 2004/0068185 | A1 | 4/2004 | Marshall |
| 2005/0062238 | A1 | 3/2005 | Broadfield |
| 2008/0228071 | A1 | 9/2008 | Mesaros |
| 2008/0234577 | A1 | 9/2008 | Murkowski et al. |
| 2011/0201927 | A1 | 8/2011 | Hayakawa |
| 2014/0142428 | A1* | 5/2014 | Kim .................... A61B 8/4405 600/437 |
| 2018/0344285 | A1* | 12/2018 | Zhao ..................... A61B 8/00 |

FOREIGN PATENT DOCUMENTS

| | | |
|---|---|---|
| KR | 20090070584 A | 7/2009 |
| WO | 2005074806 A1 | 8/2005 |

* cited by examiner

ULTRASOUND SYSTEM CONTROL PANEL AND DISPLAY LIFT

The present application is a continuation of U.S. patent application Ser. No. 15/341,065 filed Nov. 2, 2016, which is a continuation of U.S. patent application Ser. No. 14/652,858 filed Jun. 17, 2015, which is the U.S. National Phase application under 35 U.S.C. 371 of International Application PCT/IB2013/060993, filed Dec. 16, 2013, which claims the benefit of U.S. Provisional Application Ser. No. 61/739,529 filed Dec. 19, 2012. These applications are hereby incorporated by reference herein.

This invention relates to medical diagnostic ultrasound systems and, in particular, to ultrasound system carts with adjustable control panel and display elevation.

Cart-borne ultrasound systems are convenient medical imaging instruments because they can be set up easily in an imaging lab or rolled to a patient's bedside when needed. They are conventionally used by sonographers in different postures: standing, sitting or leaning over the patient being scanned. In any of these positions it is important to position the control panel in a so-called "user zone" for the sonographer so that it is comfortably accessible and enables easy manipulation of the display screen so that it can closely observed while scanning. In order to make these adjustments it is necessary for the control panel and system display to have a wide range of motion, both horizontally and vertically. After the control panel and display are properly positioned, the control panel must remain solidly in place and not move or wobble as the sonographer manipulates the controls. The present invention is directed to meeting these objectives.

In accordance with the principles of the present invention, a lift is provided for an ultrasound system which enables the control panel and display to be elevated to different heights and pivoted to a comfortable position for the sonographer. The lift allows the control panel to be positioned manually with a handle on the control panel, with the weight of the control panel offset by a hydraulic strut in the lift. The lift contains a four-bar linkage which maintains the inclination of the control panel as it is elevated and/or rotated. When the control panel is in the desired position the hydraulic strut and pivot axis are locked by solenoids to maintain the control panel solidly in position. For safety, the lift is locked while the cart is wheeled to a different position or location.

Figure 1:
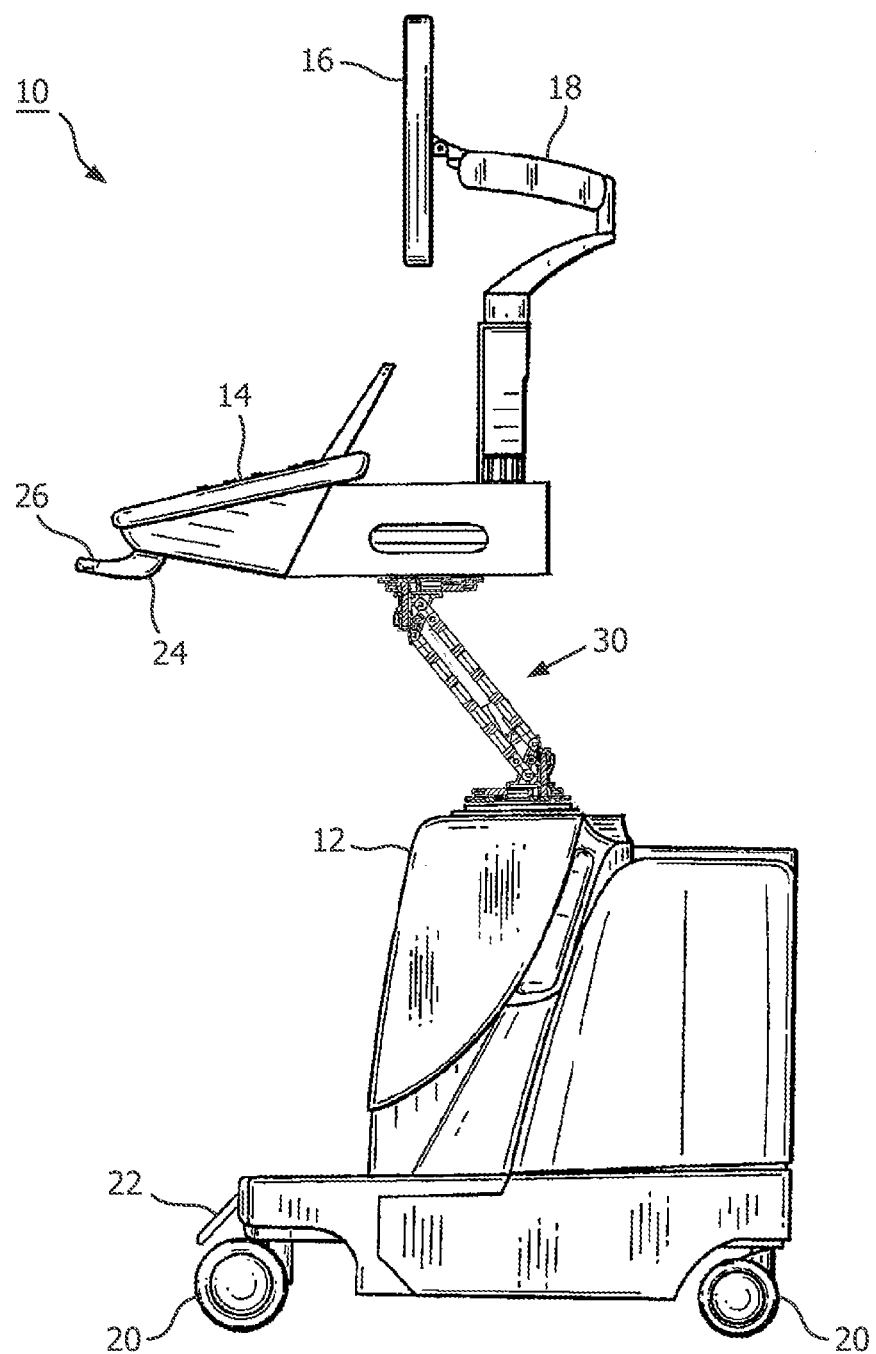
FIG. 1 illustrates a cart-borne ultrasound system constructed in accordance with the principles of the present invention.

Referring first to FIG. 1, a cart-borne ultrasound system 10 is shown. The base of the cart is a housing 12 containing the electronics of the ultrasound system such as printed circuit boards. At the back of the housing is a compartment in which accessories such as probes, video recorders, gel bottles and cables may be stored or installed. The cart has wheels 20 so that the cart can be rolled to where it is needed. In the center of the cart between the wheels is a brake pedal 22 which a user can depress the lock the wheels so that the cart will not roll or move after it has been positioned for an exam.

Above the housing 12 is a control panel 14 by which a sonographer operates the ultrasound system and controls a scanning procedure. A display screen 16 is mounted above the control panel where the sonographer can observe the screen while manipulating the controls of the control panel or scanning the patient. The display screen is mounted at the end of an articulating arm 18 which allows the screen to be raised, lowered, tilted, and moved or turned to the left or right so as to locate the screen in a convenient position for observation while scanning. The articulating arm is more fully described in US pat. pub. no. US 2008/0234577 (Murkowski et al.) In accordance with the present invention, the control panel 14 and display 16 are attached to the top of a lift 30 which is mounted on the cart housing 12. The lift enables the control panel and display to be raised, lowered, turned left and right, and swung to one side or the other of the base of the cart. This range of motion allows a sonographer to position the control panel and display where it is most convenient to operate the controls and see the ultrasound image on the screen while scanning the patient. The lift 30 is constructed as a four-bar linkage which maintains the user zone at a fixed inclination as they are moved. The user zone is positioned by the sonographer by grasping a handle 24 at the front of the control panel while depressing a release button 26 on the handle. The release button is a lighted switch mounted in the center of the handle. Depressing the release button causes it to light and releases a number of mechanisms in the mechanism arm as described below which allow the arm to be raised or lowered and rotated about either end of the arm. After the sonographer has the user zone in a desired position the sonographer releases the button 26 and the mechanism locks solidly in its current position. The sonographer can then scan the patient without causing any further motion or wobbling of the user zone.

Figure 2:
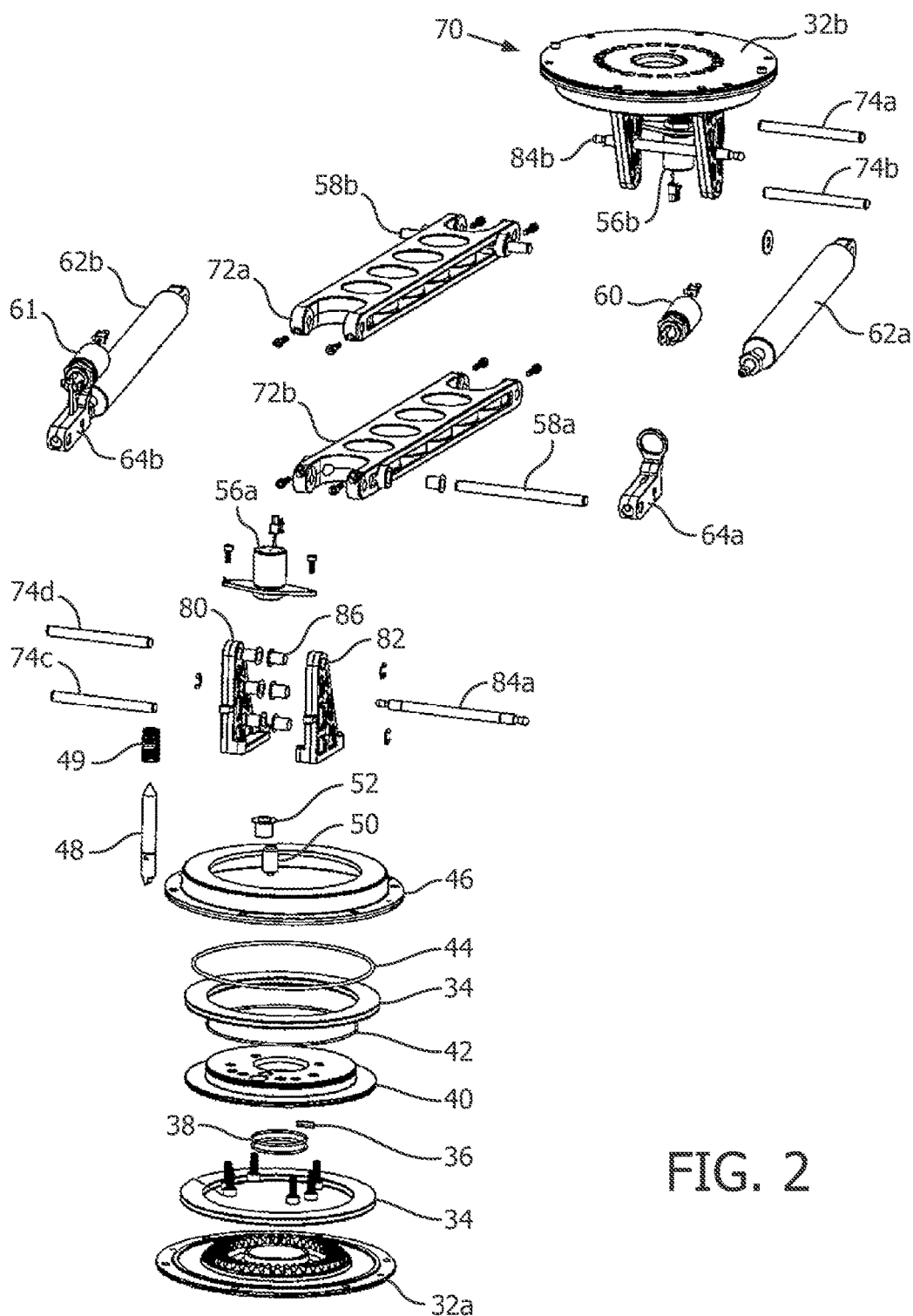
FIG. 2 illustrates an exploded view of a control panel lift for an ultrasound system of the present invention.

FIG. 2 is an exploded view of the components of the lift 30 of FIG. 1. Identical pivot elbows 70 are located at the top and bottom of the lift. Each elbow has a base plate 32a, 32b which attach to the housing and control panel assembly, respectively. Each base plate supports and centers axial journal bearings which keep the elbow assemblies in axial alignment. Each axial bearing is formed by a central annular projection from a bearing hub 40 into the center aperture of base plate 32. Thrust bearings 34 bear the weight of the control panel and display and allow them to be rotated. Each base plate has a circular arrangement of teeth which are engaged by a solenoid-controlled pin 48 to lock the mechanism in its current rotated orientation. The pin 48 is mounted in a guide bearing 52 and urged into engagement with the gear teeth by a compression spring 49. A rotation stop 36 is located in each elbow to limit the rotation to 360°. Each elbow has a bearing hub 40 with one or more detent divots in its surface. One of the divots marks the straight-ahead position of the control panel with respect to the housing, when the control panel is facing in alignment with the wheels. A ball plunger 50 drops into the straight-ahead divot in the bearing hub when the control panel is in the straight-ahead position, giving the sonographer the tactile feel of a detent when the control panel is so positioned. Completing the elbow assembly are O-rings 38, 42, and 44.

Mounted on the bearing hub 40 of each base plate are a pair of elbow frames 80 and 82. The elbow frames each support three pivot shafts, shafts 84a and 84b for mounting covers 90 for the elbows, and shafts 74a, 74b, 74c and 74d for mounting links 72a and 72b which form the arm of the mechanism. The shafts are mounted by shaft bearings 86 so that they can turn freely in the frames. The shafts 74a, 74b, 74c and 74d and links 72a and 72b are assembled to form a 4-bar linkage which, like a parallelogram, keeps the elbows oriented upward and downward as the elevation of the mechanism is adjusted. This maintains the inclination of the user zone with respect to the floor. Mounted on each side of the links 72a, 72b on pivot shafts 58a and 58b are hydraulic struts 62a and 62b. The struts may be gas or fluid struts and operate to support the weight of the control panel and display assembly, offsetting virtually all of its weight as they are repositioned by a sonographer. A release housing 64a, 64b is mounted at the end of the piston of each strut and a solenoid 60, 61 is mounted on each release housing to lock the strut in its present piston extension. When the sonographer depresses the button 28 on the control panel handle, the solenoids 60, 61 are energized, opening a valve in each strut so that gas or fluid in each strut can flow as the user zone elevation is adjusted. When the button is released and the solenoids are no longer energized, the valves are closed which act as a brake to lock the struts in their current piston-extended positions.

Solenoids 56a and 56b are mounted in the elbows to control the pin 48 in each elbow. When solenoids 56a and 56b are energized by the depression of button 28, the pins 48 are pulled out of engagement with the teeth in each elbow, permitting the elbow assemblies 70 to rotate freely. After the sonographer has turned the control panel to its desired orientation, the button 28 is released and the pins 48 drop into the teeth, locking the elbows and preventing any further rotation by both elbows. The user zone rotation and elevation are then securely locked in position.

In accordance with a further aspect of the present invention, a switch is in-line between the button and the four solenoids. This switch is closed when the wheel brake 22 is depressed to lock the wheels, and is open when the wheel brake 22 is released to roll the cart. This means that the solenoids of the lift can only be energized to adjust the elevation and rotation of the lift when the brake 22 is engaged to lock the wheels 20. When the brake 22 is released to roll the cart, the solenoids cannot be energized and the lift is locked in position. This prevents the lift, control panel and display from swinging around or moving as the cart is rolled from place to place, ensuring that they are locked in position when the cart moves. This feature prevents injury to the operator or other personnel as well as damage to the ultrasound system or other objects.

In accordance with a further aspect of the present invention, a switch is located in the straight-ahead detent of each of the bearing hubs and coupled to the brake 22. This switch controls a solenoid in the brake release of the brake 22 and is arranged so that the brake cannot be released to roll the wheels unless each ball plunger 50 is engaged in its straight-ahead detent and the control panel and display are positioned in their straight-ahead position. This ensures that the weight of the control panel and display are centered with respect to the housing as the cart is moved, which is easier and more convenient for most users to manipulate.

Figure 3:
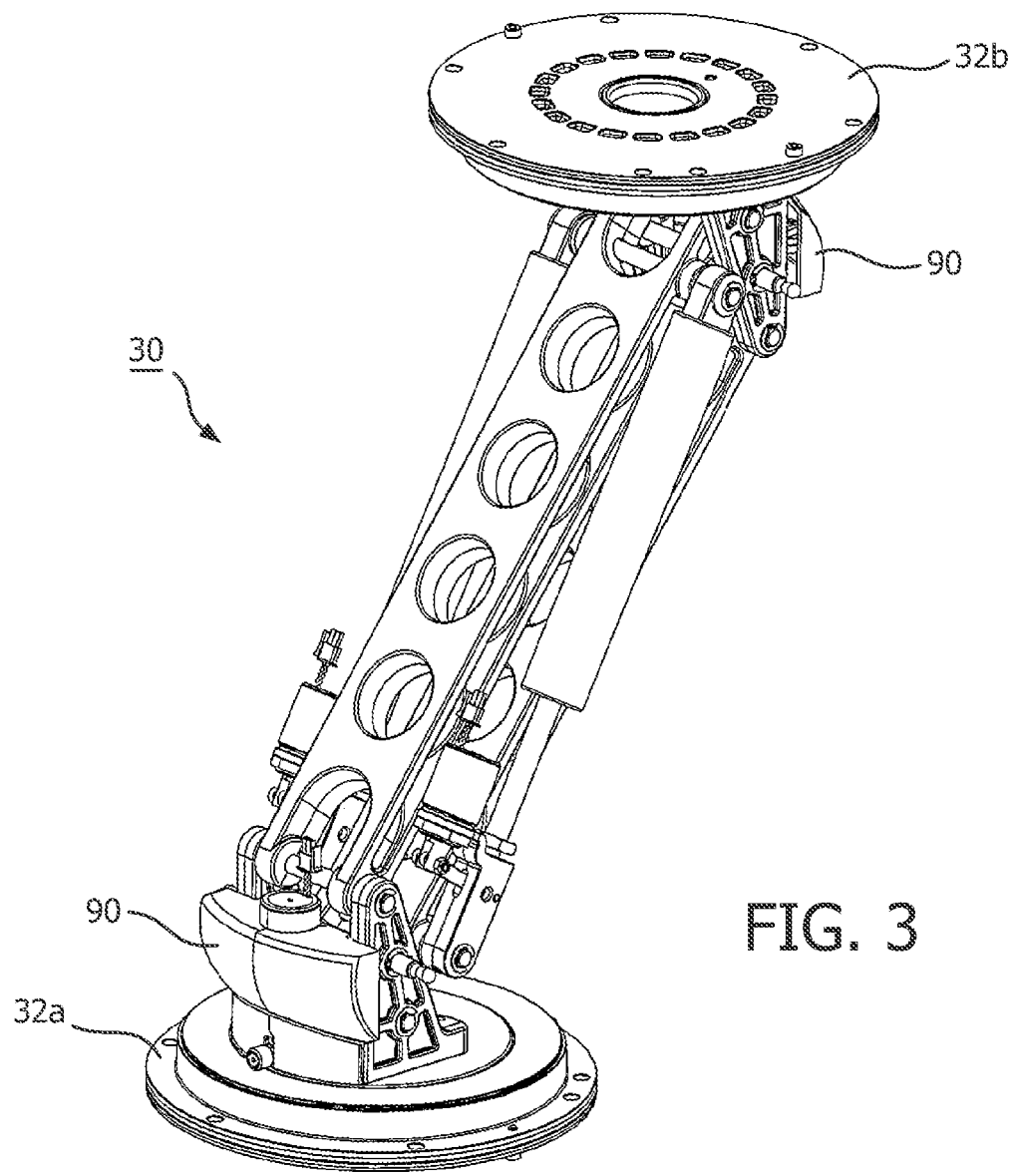
FIG. 3 is a perspective view of the assembled control panel lift of FIG. 2.

FIG. 3 illustrates the lift 30 of FIGS. 1 and 2 when fully assembled and in a slightly lowered elevation. It can be seen that the upper and lower surfaces of the elbow plates 32a and 32b remain parallel to each other. This view shows the elbow covers 90 mounted on their mounting pins 84a and 84b.

Figure 4:
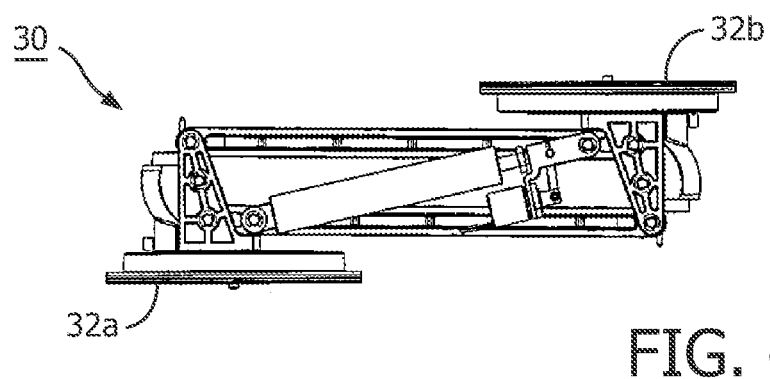
FIG. 4 illustrates the control panel lift of FIG. 3 in its fully folded position.

FIG. 4 shows the lift of FIG. 3 when fully lowered. It is seen that the surfaces of the elbow plates 32a and 32b remain parallel in this and all other positions of the lift 30.

What is claimed is:

1. An ultrasound system comprising:
   a cart housing comprising wheels;
   a control panel;
   a lift coupling the cart housing to the control panel, wherein the lift comprises an elevation mechanism configured to change a position of the control panel in relation to the cart housing;
   a control button configured to be actuated by a user to allow the elevation mechanism to change the position of the control panel; and
   a switch configured to lock the lift in position when the wheels are locked, when the control panel is located in a straight-ahead position, or a combination thereof.

2. The system of claim 1, comprising a pivot elbow configured to rotate in relation to the control panel.

3. The system of claim 2, comprising: a first solenoid coupled to the pivot elbow; and a second solenoid coupled to a hydraulic strut in the elevation mechanism, wherein the first and second solenoids are configured to be actuated by the control button to enable the pivot elbow to rotate and a piston of the hydraulic strut to extend or retract.

4. The system of claim 3, wherein the pivot elbow is located at the bottom of the lift and is coupled to the cart housing, and the system further comprises a second pivot elbow coupled to the control panel.

5. The system of claim 4, wherein the elevation mechanism comprises a four-bar linkage coupled between the first and second pivot elbows, wherein the four-bar linkage operates to maintain a relative inclination between the first and second pivot elbows.

6. The system of claim 3, wherein the switch is coupled in-line between the control button and the first and second solenoids.

7. The system of claim 6, wherein, when the brake is actuated to lock the wheels, the switch is closed to allow the first and second solenoids to be energized by the control button.

8. The system of claim 2, wherein the cart housing comprises a brake configured to be actuated by the user to lock the wheels.

9. The system of claim 8, wherein, when the brake is not actuated, the pivot elbow and elevation mechanism are locked.

10. The system of claim 8, wherein the pivot elbow comprises the switch, which is coupled to the brake.

11. The system of claim 2, wherein the pivot elbow comprises gear teeth, and a solenoid actuated pin which engages the gear teeth to prevent rotation of the pivot elbow.

12. The system of claim 2, wherein the pivot elbow further comprises a detent which is engaged when the control panel is oriented in the straight-ahead position.

13. The system of claim 1, wherein the elevation mechanism comprises a first hydraulic strut and a second hydraulic strut, the second hydraulic strut coupled to the four-bar linkage.

14. The system of claim 1, wherein the elevation mechanism comprises a four-bar linkage.

15. The system of claim 1, wherein the control panel comprises a handle and the control button is located on the handle.

16. The system of claim 1, wherein the switch is configured to determine when the control panel is located in the straight-ahead position, and wherein the brake cannot be operated to unlock the wheels unless the control panel is determined to be in the straight-ahead position.

17. The system of claim 1, further comprising a display coupled above the control panel.

18. The system of claim 1, wherein the system is configured such that the control panel can be articulated by the lift to be oriented in the straight-ahead position.

19. The system of claim 1, wherein the control button comprises a lighted switch.

\* \* \* \* \*